United States Patent [19]

Jekkel née Bokány et al.

[11] Patent Number: 5,156,960

[45] Date of Patent: Oct. 20, 1992

[54] MICROBIAL PROCESS FOR THE PRODUCTION OF IMMUNOSUPPRESSIVE ANTIBIOTICS

[75] Inventors: Antónia Jekkel née Bokány; Gábor Ambrus; Éva Tóth-Sarudy; István Mihály; Ágota Hülber née Dobos; Attila Andor; Károly Albrecht; Kálmán Könczöl; Valéria Széll; Éva Tomori née Joszt; Imre Moravcsik, all of Budapest; Kálmán Pólya, Debrecen; János Erdei, Debrecen; Lajos Kiss, Debrecen; Béla Makádi, Debrecen; Károly Nagy, Debrecen; Béla Palotás, Debrecen; Etelka Deli née Konszky, Debrecen; Károly Buzási, Debrecen; Anikó Molnár née Antal, Debrecen; György Sántha, Debrecen; Vilma Szászhegyesi, Debrecen, all of Hungary

[73] Assignee: Biogal Gyogyszergyar, Debrecen, Hungary

[21] Appl. No.: 454,005

[22] Filed: Dec. 20, 1989

[30] Foreign Application Priority Data

Dec. 20, 1988 [HU] Hungary .................. 6497/88

[51] Int. Cl.$^5$ .................. C12P 21/04; C12R 1/645; A61K 37/00
[52] U.S. Cl. .................. 435/71.1; 435/71.3; 435/254; 435/911; 514/11; 530/317; 530/321
[58] Field of Search .................. 435/71.1, 71.3, 911, 435/254; 514/11; 530/317, 321

[56] References Cited

U.S. PATENT DOCUMENTS

| | | | |
|---|---|---|---|
| 4,215,199 | 7/1980 | Harri et al. | 435/71.1 |
| 4,288,431 | 9/1981 | Traber et al. | 514/11 |
| 4,289,851 | 9/1981 | Traber et al. | 435/71.1 |
| 4,764,503 | 8/1988 | Wenger | 514/11 |

*Primary Examiner*—Herbert J. Lilling
*Attorney, Agent, or Firm*—Keil & Weinkauf

[57] ABSTRACT

The invention relates to a microbial process for the production of immunosuppressive cyclosporine antibiotic complex or of its components, cyclosporine A, cyclosporine B and cyclosporine C, by the aerobic fermentation of a filamentous fungus strain biosynthesizing the above antibiotic(s) in a nutrient medium containing utilizable carbon and nitrogen sources as well as mineral salts, and by isolating the products formed, which comprises culturing a strain of the novel *Tolypocladium varium* fungus species producing the cyclosporine antibiotic complex, preferably *tolypocladium varium* sp. nov. CY/93, deposited at the National Collection of Agricultural and Industrial Microorganisms, Budapest, Hungary under the number NCAIM(P)F 001005, on a nutrient medium containing carbon sources, organic and inorganic nitrogen sources as well as mineral salts, under aerobic conditions, at 25° to 30° C., and, if desired, isolating and purifying the cyclosporine antibiotic complex or its components produced.

2 Claims, No Drawings

MICROBIAL PROCESS FOR THE PRODUCTION OF IMMUNOSUPPRESSIVE ANTIBIOTICS

This invention relates to a microbial process for the production of a cyclosporine complex or of its components cyclosporine A, cyclosporine B and cyclosporine C by aerobic fermentation.

The cyclosporines are cyclic, neutral, apolar eleven-membered oligopeptides wherein some of the amino acid moieties are different. Cyclosporine A and cyclosporine B were isolated first by A. Rüegger et al. (Helv. Chim. Acta 59, 1075 (1976)), while cyclosporines B, D, E and G by R. Traber et al. (Helv. Chim. Acta 60, 1968 (1977)) from the culture of a fungus (NRRL 8044), identified earlier as *Trichoderma polysporum* (Ling ex Pers.) Rifai. Later on the taxonomy of the strain mentioned was revised and it was described thereafter as *Tolypocladium inflatum* Gams in the literature.

At present 25 different cyclosporine antibiotics, listed as cyclosporines A to Z, are known (Helv. Chim. Acta 70, 13 (1987)). Among these components cyclosporine A is the most valuable substance having a selective immunosuppressive effect.

Cyclosporine A became first known as a mild antifungal antibiotic, its significant immunosuppressive effect was recognized only later (J. F. Borel et al.: Immunology 32, 107 (1977)).

It was confirmed in a series of in vitro and in vivo assays that cyclosporines A, C and G are very specific immunosuppressive agents.

Cyclosporine A inhibits both humoral and cell mediated immune response. With respect to its mode of action, it inhibits T cell proliferation as well as interleukin-2 synthesis.

The therapeutic use of cyclosporine A in human organ transplantations was reported in 1978. It was first applied in kidney (R. J. Calne et al.: Lancet 1978/2, 1323) and bone marrow (R. L. Powles et al.: Lancet 1978/2, 1327) transplantations.

In the course of organ (kidney, pancreas, liver, heart, lung) and bone marrow transplantations the rejection of organs or bone marrow may be suppressed by the application of cyclosporine A.

Furthermore, cyclosporine A was successfully applied for the treatment of some autoimmune diseases (uveitis, rheumatoid arthritis, psoriasis and myasthenia gravis).

In the patent literature the following microorganisms were used for the production of the cyclosporine complex: *Cylindrocarpon lucidum* Booth, NRRL 5760 (Swiss patent specification No. 589,716); *Tolypocladium inflatum* Gams, NRRL 8044 (according to earlier taxonomy: *Trichoderma polysporum* (Link ex Pers.) Rifai (Swiss patent specification No. 603,790), according to Bisett (1983), *Tolypocladium inflatum* Gams, 1971 is synonymous with *Tolypocladium niveum* (Rostrup) Bisett comb. nov., and *Fusarium solani*, MCI-1549, MCI-1550 (published Japanese patent application No. 82 63093). In the course of fermentation processes carried out with the above microorganisms low production levels for the cyclosporines were obtained after long fermentation periods and the yields of isolation were also low.

Our investigations were focussed to find microorganism strains which would produce the cyclosporine antibiotic complex or its components in higher concentrations and at more advantageous conditions than the former strains. Screening a great number of filamentous fungus strains isolated from soil a microorganism strain of the Tolispocladium genus was found which was able to biosynthesize the cyclosporine antibiotic complex. This microorganism, assigned CY/93, could not be identified in taxonomic studies with any of the cyclosporine complex-producer fungus species. *Tolypocladium varium* species nova CY/93 is a new taxon of the Tolypocladium genus which can be differentiated on the species level.

Based on the above findings the invention relates to a microbial process yielding a broth containing high concentrations of cyclosporine, by applying a new microorganism, *Tolypocladium varium* species nova CY/93, deposited at the National Collection of Agricultural and Industrial Microorganisms, Budapest, Hungary under the number NCAIM(P)F 001005. In addition to the main product, cyclosporine A, the fermentation broth also contains small amounts of cyclosporine B and cyclosporine C.

The taxonomic features of the new fungus species were compared to the main diagnostic properties of Tolypocladium species as follows:

The Tolypocladium genus was first described by Gams in 1971 as a new genus of soil Moniliales. Its characteristic properties are: slow growth, pillow-like white colonies, terminal and lateral phialides developed partly on a short side-branch, with strongly swollen base and filamentous, frequently bowed neck, ending in a unicellular conidium. Within this genus the following 3 novel species were differentiated by Gams: *T. geodes*, *T. cylindrosporum* and *T. inflatum*. *T. geodes* has pronounced Actinomycetes-type soil odor while the new *T. varium* sp. nov. CY/93 is completely devoid of it. Furthermore, the carrier cells of *T. geodes* are significantly narrower than those of *T. varium* sp. nov. CY/93. The conidia of *T. cylindrosporum* are characteristically long and elongated while those of T. varium sp nov. CY/93 are spherical and only slightly elongated. The conidia of *T. inflatum* are ovoid and longer than those observed in the culture of *T. varium* sp. nov. CY/93. The phialides of *T. inflatum* are characteristically produced in verticils either directly on the hyphae or on 2 to 3 $\mu$m long carrier cells. *T. varium* sp. nov. CY/93 shows no such pattern of verticillate arrangement, this is only detectable from time-to-time sporadically. Due primarily to the white cotton-like aerial mycelium, the colonies of all known Tolypocladium species are white, while the reverse of the colonies is yellowish-gray, colorless or yellow. No typical soluble pigments are produced. *T. varium* sp. nov. CY/93 may be differentiated also in this respect: on media containing glucose and peptone as well as malt extract, yeast extract, a dark, deep gray to black pigment is produced with temporal variability.

The taxonomic evaluation of the new species compared to the other known Tolypocladium species was performed on the basis of the following publications: W. Gams: Persoonia, 6, 185–191 (1971); G. L. Barron: Can. J. Bot. 5R, 439–442 (1980), and Bisett, J. Can. J. Bot. 61, 1311–1329 (1983).

The diagnostic patterns of *Tolypocladium varium* sp. nov. CY/93 are summed up in the following.

Ten-day old colonies have a diameter of 10 to 25 mm, their surface is covered by white, cotton-like, richly sporulating aerial mycelium. The reverse of the colonies is yellowish-grey or dirty grey. In some complex media a dark grey soluble pigment is produced. Both terminal and lateral sporulation is observed on the hyphae of the aerial mycelium. Phialides are located either solitarily or sporadically, occasionally in verticils, directly on the hyphae or on short (2 to 3 μm) carrier cells. The phialides are built up from a swollen base (2–4×2–3 μm) and a long, filamentous neck (2–4×0-.5–0.6 μm). The conidia of the heads are small (2–3×1-.3–2.2 μm), usually spherical and smooth. The specific epithet "varium" refers to the variability of the phialides. *Tolypocladium varium* shows in its life cycle a certain similarity to the genus Harposporium, about which more is referred to elsewhere. The CY/93 strain cannot utilize raffinose, but it grows well on the following carbon sources: mannitol, inositol, saccharose, fructose, rhamnose, galactose, dextrose, arabinose and xylose in surface culture. Its cultures are poorly developed on nutrient and malt-extract agar, and well developed on soyameal agar, Czapek agar and potato-dextrose agar. The oatmeal agar and the dextrose yeast extract agar are not suitable for storage.

*Tolypocladium varium* differs from *Tolypocladium trigonsporum* which produces triagonal conidia on the upper surface and which has slightly concave edges. *Tolypocladium varium* also differs from *Tolypocladium balanoidines*, the latter producing lageniform lateral phialides. Moreover, the holotype strain (CY/93) of *Tolypocladium varium* sp. nov. is different from the authentic type strain of *Tolypocladium inflatum* (CBS 714.70) in the respect that the latter strain develops a rich white aerial mycelia when cultured on maltose-agar nutrient medium, while *Tolypocladium varium* sp. nov. CY/93 does not produce such aerial mycelia. The type strain of *Tolypocladium inflatum* produces reddish brown endopigment in its substrate mycelia on iron-peptone agar culture medium, while the substrate mycelia of *Tolypocladium varium* sp. nov. CY/93 remains light yellow. Strain *Tolypocladium varium* sp. nov. CY/93 does not utilize arabinose, while *Tolypocladium inflatum* does. Upon utilizing sodium nitrite the latter strain develops rich mycelia, while *Tolypocladium varium* sp. nov. CY/93 hardly grows.

The comparison of *Tolypocladium varium* sp. nov. CY/93 with authentic strains of other Tolypocladium species, with *Trichoderma polysporum* ATCC 16,641 and with *Cylindrocarpon lucidum* NRRL 5760 is summarized in Table I.

Based on the above findings, the invention relates to a process for the preparation of the cyclosporine antibiotic complex and/or of its components, cyclosporine A, cyclosporine B and cyclosporine C, by the aerobic fermentation of a filamentous fungus strain biosynthesizing the above antibiotic(s) in a nutrient medium containing utilizable carbon and nitrogen sources as well as mineral salts, and by isolating the products formed, which comprises cultivating a strain of the novel *Tolypocladium varium* fungus species producing the cyclosporine antibiotic

TABLE I

| | Tolypocladium varium CY/93 | Tolypocladium cylindrosporum CBS 717.70 | Tolypocladium cylindrosporum CBS 718.70 | Tolypocladium geodes CBS 721.70 | Tolypocladium geodes 722.70 | Trichoderma polysporum ATCC 16641 | Cylindrocarpon lucidum NRRL 5760 |
|---|---|---|---|---|---|---|---|
| Cellulose decomposition | − | − | − | − | − | +++ | +++ |
| Aerial mycelia: green or bluish green | − | − | − | − | − | +++ | +++ |
| Red soluble pigment production on King-agar | − | − | − | − | − | − | +++ |
| Brown pigment production on iron-peptone agar | − | − | − | − | − | − | +++ |
| Dark brown pigment production on synthetic glycerol agar | − | − | − | − | − | +++ | − |
| Saccharose utilization | +++ | +++ | +++ | +++ | +++ | − | +++ |
| Inuline utilization | − | − | − | − | − | − | +++ |
| Growth at 5° C. | +++ | +++ | +++ | +++ | +++ | − | − |
| Growth at 37° C. | − | − | − | − | − | + | +++ |
| Resistance against heat-treatment at 50° C. for 60 minutes | +++ | − | − | − | − | +++ | +++ |
| Acid production from glucose | +++ | +++ | ± | ± | +++ | +++ | +++ |
| Sodium salicilate utilization | − | − | − | − | − | +++ | +++ |
| Sodium malonate utilization | ++ | ++ | ++ | − | − | ++ | ++ |
| Sodium tartarate utilization | + | ++ | ++ | − | − | ++ | ++ |
| Lilac soluble pigment | − | − | − | +++ | +++ | − | − |

TABLE I-continued

| Tolypocladium varium CY/93 | Tolypocladium cylindrosporum CBS 717.70 | Tolypocladium cylindrosporum CBS 718.70 | Tolypocladium geodes CBS 721.70 | Tolypocladium geodes 722.70 | Trichoderma polysporum ATCC 16641 | Cylindrocarpon lucidum NRRL 5760 |
|---|---|---|---|---|---|---|
| production on tyrosine and leucine agar | | | | | | | complex, preferably Tolypocladium varium sp. nov. cy/93, deposited at the National Collection of Agricultural and Industrial Microorganisms, Budapest, Hungary under the number NCAIM(P)F 001005, on a nutrient medium containing carbon sources, organic and inorganic nitrogen sources as well as mineral salts, under aerobic conditions, in a temperature range of 25° to 30° C. and, if desired, isolating and purifying the cyclosporine antibiotic complex or its components produced.

According to a preferred embodiment of the present invention the cyclosporine antibiotic complex is produced with the new Tolypocladium varium sp. nov. CY/93 strain. The selected strain is highly advantageous due to its fast growth. It is a favorable feature that the strain can utilize saccharose, glucose, sorbose, maltose, fructose, starch, glycerol as well as various fats and oils as carbon sources, and a variety of organic and inorganic nitrogen sources, such as corn steep liquor, peptone, yeast extract, meat extract, sodium nitrate, ammonium nitrate, ammonium sulfate as well as various amino acids. In addition to the above carbon and nitrogen sources the nutritive media used for the production of the cyclosporine antibiotic complex may also contain mineral salts (potassium chloride, magnesium sulfate or potassium dihydrogen phosphate), trace elements (copper, manganese, iron salts), furthermore vitamins and antifoam agents.

According to a preferred method of the present invention a liquid medium is inoculated with a suspension of conidia and mycelia, prepared from the agar slant culture of Tolypocladium varium sp. nov. CY/93. After cultivating for 3 days, the pre-culture obtained is used to inoculate the medium applied for the antibiotic production, which is thereafter incubated at 25° to 30° C., preferably at 25° C., for 5 to 7 days. During the fermentation the pH is maintained in the range of 6.0 to 2.5, preferably at 5.2. Fermentation is performed under aerobic conditions, at vigorous stirring (750 to 100 r.p.m.) and aeration of 300 liters/hour.

During fermentation the cyclosporine content of the broth is monitored by microbial assay and high pressure liquid chromatography. As soon as the maximum amount of antibiotics has been produced, these are obtained from the culture liquor in known manner of extractive and/or adsorptive methods.

The cyclosporine concentration of the broths is measured on the basis of the antifungal activity of cyclosporines by plate diffusion test. Aspergillus niger, Aspergillus japonicus and Curvularia lunata may advantageously be used as test organisms (M. Dreyfuss et al.: European J. Appl. Microbiol. 3., 125-133 (1976)). The HPLC analysis of the cyclosporine concentration of the broth was carried out from the broth samples diluted tenfold with methanol according to F. Kreuzig (J. Chromat. 290, 181 (1984)). According to our experiments the cyclosporine antibiotic complex, containing cyclosporine A as main product and cyclosporine B and cyclosporine C as minor components, is produced in high yield (950 μg/ml) by the novel Tolypocladium varium sp. nov. CY/93 strain.

Extraction methods may be advantageously applied for the isolation of the cyclosporine complex from the fermentation broth. Before extraction the mycelium is separated either by filtering or centrifuging. Antibiotics produced during fermentation may advantageously be washed out from the microorganism cells with lower alkanols, preferably with methanol, or with organic ketones, preferably with acetone, while the cyclosporines in the broth filtrate may be extracted with water-immiscible organic solvents, such as ethyl acetate, n-butyl acetate, dichloromethane, 1,2-dichloroethane or chloroform, preferably with n-butyl acetate. The raw product obtained by extraction is contaminated by red and violet pigments, produced by the fungus, which may be removed by adsorption on active charcoal or silica gel. Possible lipid contaminants (i.e. antifoam agent) may be separated by distribution in a system of petroleum ether and methanol containing 10% of water, where the impurities are transferred into the petroleum ether phase.

The aqueous methanol phase is concentrated at reduced pressure, then the aqueous residue is extracted with dichloromethane, which is evaporated to yield purified cyclosporine. Cyclosporine A may be separated from the minor cyclosporine components by column chromatography and recrystallization.

The structure of the isolated products was elucidated by UV, IR, $^1$H NMR, $^{13}$C NMR and mass-spectroscopy and amino acid analysis.

The following examples are for purposes of illustration and do not limit the scope of the invention.

EXAMPLE 1

A conidium and mycelium suspension is prepared with 5 ml of a 0.9% sodium chloride solution obtained from the malt extract-yeast extract agar slant culture of Tolypocladium varium sp. nov. CY/93. One ml of this suspension is used to inoculate 100 ml of sterile IC inoculum medium in a 500 ml Erlenmeyer flask.

| Composition of the IC medium: | |
|---|---|
| Glucose | 40 g |
| Casein-peptone | 5 g |
| Sodium nitrate | 3 g |
| Potassium dihydrogen phosphate | 2 g |
| Potassium chloride | 0.5 g |
| Magnesium sulfate × 7 H$_2$O | 0.5 g |
| Iron(II) sulfate × 7 H$_2$O | 0.01 g |
| in 1000 ml of tap water. | |

The pH of the nutritive medium is adjusted to 5.2 before sterilization and the mixture is sterilized at 121° C. for 25 min. The culture is incubated at 25° C. on a rotary shaker (340 r.p.m.), then 5 ml portions of this inoculum medium are used to inoculate fifteen 500-ml Erlenmeyer flasks containing 100 ml of FC$_1$ sterile media each.

| Composition of the FC₁ medium: | |
| --- | --- |
| Glucose | 80 g |
| Tryptone | 40 g |
| Urea | 2 g |
| Ammonium sulfate | 12 g |
| Sodium nitrate | 3 g |
| Potassium dihydrogen phosphate | 2 g |
| Potassium chloride | 0.5 g |
| Magnesium sulfate × 7 H$_2$O | 0.5 g |
| Iron(II) sulfate × 7 H$_2$O | 0.01 g |
| in 1000 ml of tap water. | |

The pH of the nutritive medium is adjusted to 5.2 before sterilization and the mixture is sterilized at 121° C. for 25 min.

The flasks are incubated on a rotary shaker (340 r.p.m.) at 25° C. During fermentation the antibiotic concentration of the broth is monitored by plate diffusion test. *Aspergillus niger* is applied as the test organism. The concentration of the cyclosporine antibiotic complex in the broth is assayed using cyclosporine A as standard.

Fermentation is continued for 168 hours, when the broth contains 400 μg/ml of cyclosporine antibiotic complex. The cyclosporine complex is isolated according to the following method.

The cells of one liter of the broth are filtered and the antibiotics are washed off twice with 200 ml of methanol. The aqueous methanol solution is concentrated under reduced pressure, then the antibiotic complex is extracted from the aqueous concentrate with 2×50 ml of n-butyl acetate. The cyclosporine content of the broth filtrate is extracted with 200 ml of n-butyl acetate. The n-butyl acetate extracts are pooled, dried over anhydrous sodium sulfate, then evaporated at reduced pressure at 40° C. The 3.7 g of raw product obtained are dissolved in 10 ml of methanol and transferred on top of a gel column of Sephadex LH-20 (column length 40 cm, diameter 2.5 cm) prepared with methanol. Then the lipid impurities are separated by eluting with methanol. The fractions containing the cyclosporine complex are evaporated under reduced pressure at 40° C. The separation of the components of the cyclosporine complex obtained (1.05 g) is performed by chromatography on a silica gel column prepared from 20 g of Kieselgel 40 (Reanal, Budapest), by eluting with chloroform-methanol solvent mixtures containing gradually increasing volumes of methanol. Elution is started with 100 ml of chloroform, then it is continued with chloroform-methanol mixtures wherein the methanol content of each 100 ml portion is increased by 0.5%. The cyclosporine content of the fractions is monitored by thin-layer chromatography (plate: Kieselgel 60 F$_{254}$, DC Alufoil/Merck/, developing solvent: ethyl acetate-isopropanol 95:5, detection: iodine vapours). Cyclosporines A, B and C are eluted from the column by methanol-chloroform mixtures containing 2.0%, 2.5% and 3.0% of methanol, resp. Fractions containing the pure components are evaporated under reduced pressure, yielding 225 mg of cyclosporine A (m.p.: 137°–140° C., [α]$_D$: −189° /methanol/), 25 mg of cyclosporine B (m.p.: 149°–151° C.) and 52 mg of cyclosporine C (m.p.: 150°–152° C.).

EXAMPLE 2

Five liters of IC inoculum medium, sterilized at 121° C. for 45 minutes in a 10-liter laboratory fermentor, are inoculated with 200 ml of an inoculum shake culture prepared as described in Example 1, then incubated at 25° C., stirred at 750 r.p.m. and aerated with 300 l/h air.

Fermentation is continued for 72 hours, then 500 ml of this inculum medium are used to inoculate 5 liters of FC$_2$ medium, sterilized at 121° C. for 45 minutes in a 10-liter laboratory fermentor.

| Composition of the FC₂ medium: | |
| --- | --- |
| Glucose | 80 g |
| Tryptone | 40 g |
| Urea | 2 g |
| Ammonium sulfate | 12 g |
| Sodium nitrate | 3 g |
| Potassium dihydrogen phosphate | 2 g |
| Potassium chloride | 0.5 g |
| Magnesium sulfate × 7 H$_2$O | 0.5 g |
| Copper(II) sulfate × 5 H$_2$O | 0.01 g |
| Manganese(II) sulfate × 7 H$_2$O | 0.01 g |
| Iron(II) sulfate × 7 H$_2$O | 0.01 g |
| in 1000 ml of tap water. | |

The pH of the medium is adjusted to 5.2 before sterilization. The inoculated culture is incubated at 25° C., stirred with 750 r.p.m. and aerated with 300 l/h.

Fermentation is continued under the above conditions for 144 hours till peak cyclosporine titers are attained, then the broth is harvested.

Cyclosporine A is isolated from the 4.8 liters of the fermentation broth, containing 500 μg/ml of the cyclosporine complex, by the following method.

The cells of microorganism are centrifuged and the cyclosporine complex is washed out from the cells with 2×1 liters of methanol. The aqueous methanol solution is concentrated under reduced pressure, then the antibiotic complex is extracted from the aqueous concentrate with 2×250 ml of n-butyl acetate.

The cyclosporine complex is extracted from the filtrate of the fermentation broth with 2×500 ml of n-butyl acetate. All n-butyl acetate extracts are pooled, dried over anhydrous sodium sulfate, then the solution is evaporated under reduced pressure at 40° C. The preliminary purification of the raw product obtained (19.2 g) is performed by chromatography on a column prepared from 100 g of Kieselgel 60 (particle size 0.063 to 0.2 mm), with a developing solvent of chloroform-methanol-acetone (92:4:4). The fractions containing the cyclosporine complex (thin-layer chromatographic analysis: plate: Kieselgel 60 F$_{254}$, DC Alufoil/Merck/; developing solvent: hexane-acetone 2:1; detection: chlorine/tolidine reagent) are evaporated to dryness. The evaporation residue (5.28 g) is submitted to column chromatography to yield cyclosporine A. The column is prepared from 115 g of Kieselgel 60 (particle size 0.063 to 0.2 mm), and it is eluted with mixtures of hexane-acetone containing gradually increasing volumes of acetone. Cyclosporine A is eluted from the column with a mixture containing 23% of acetone. By evaporating the fractions containing cyclosporine A 1.46 g of cyclosporine A are obtained.

EXAMPLE 3

A conidium and mycelium suspension is prepared with 5 ml of a 0.9% sodium chloride solution from the malt extract-yeast extract agar slant culture of *Tolypocladium varium* sp. nov. CY/93 and is used to inoculate 800 ml of IC inoculum medium, described in Example 1, and sterilized in a 3-liter Erlenmeyer flask. The flask is incubated on a rotary shaker (340 r.p.m.) at 25° C. for 2.5 days, then 5 liters of an FC$_3$ medium, sterilized in a 10-liter laboratory fermentor at 121° C. for 45 minutes, are inoculated with it.

| Composition of the FC$_3$ medium: | |
|---|---|
| Sorbose | 60 g |
| Tryptone | 40 g |
| Urea | 2 g |
| Ammonium sulfate | 12 g |
| Sodium nitrate | 3 g |
| Potassium dihydrogen phosphate | 2 g |
| Potassium chloride | 0.5 g |
| Magnesium sulfate × 7 H$_2$O | 0.5 g |
| Manganese(II) sulfate × 7 H$_2$O | 0.01 g |
| Iron(II) sulfate × 7 H$_2$O | 0.01 g |
| in 1000 ml of tap water. | |

The pH of the medium is adjusted to 5.2 before sterilization. The inoculated culture is incubated at 25° C., stirred with 1000 r.p.m. and aerated with 300 l/h.

Fermentation is continued for 168 hours, when the fermentation broth contains 600 μg/ml of the cyclosporine complex according to the microbial assay.

By isolation as described in Example 2, 310 mg of cyclosporine A are obtained from 1 liter of the broth.

EXAMPLE 4

A conidum and mycelium suspension is prepared with 5 ml of a 0.9% sodium chloride solution from the 5- to 7-day old malt extract-yeast extract agar slant culture of *Tolypocladium varium* sp. nov. CY/93 (NCAIM(P)F 001005) and is used to inoculate 500 ml of IC inoculum medium described in Example 1, and sterilized in a 3-liter Erlenmeyer flask. The flask is incubated on a rotary shaker (340 r.p.m.) at 25° C. for 3 days, then 5 liters of an FC$_4$ medium, sterilized in a 10-liter laboratory fermentor at 121° C. for 45 minutes, are inoculated with it.

| Composition of the FC$_4$ medium: | |
|---|---|
| Maltose | 80 g |
| Tryptone | 40 g |
| Urea | 2 g |
| Ammonium sulfate | 12 g |
| Sodium nitrate | 3 g |
| Potassium dihydrogen phosphate | 2 g |
| Potassium chloride | 0.5 g |
| Magnesium sulfate × 7 H$_2$O | 0.5 g |
| Manganese(II) sulfate × 7 H$_2$O | 0.01 g |
| Copper(II) sulfate × 5 H$_2$O | 0.01 g |
| Iron(II) sulfate × 7 H$_2$O | 0.01 g |
| in 1000 ml of tap water. | |

The pH of the medium is adjusted to 5.2 before sterilization.

After inoculation the fermentation broth is incubated at 25° C., stirred at 1000 r.p.m. and aerated with 300 l/h.

Fermentation is continued for 144 hours, when the fermentation broth contains 620 μg/ml of the cyclosporine complex according to the microbial assay.

Isolation is performed by the method described in Example 1. Thus 305 mg of cyclosporine A were obtained from 1 liter of broth.

EXAMPLE 5

A conidum and mycelium suspension is prepared with 5 ml of a 0.9% sodium chloride solution from the 5-to 7-day old malt extract-yeast extract agar slant culture of *Tolypocladium varium* sp. nov. CY/93 (NCAIM(P)F 001005), and is used to inoculate 500 ml of IC inoculum medium described in Example 1, and sterilized in a 3-liter Erlenmeyer flask. The flask is incubated on a rotary shaker (340 r.p.m.) at 25° C. for 2 days, then 5 liters of an FC$_1$ medium, sterilized in a 10-liter laboratory fermentor at 121° C. for 45 minutes, are inoculated with it. After inoculation the fermentation broth is stirred with 750 r.p.m. at 25° C. and aerated with 300 l/h. After cultivating for 96 hours a sterilized aqueous solution of 100 g of maltose is added and the fermentation is continued till the 144th hour when the broth contains 950 μg/ml of the cyclosporine complex according to the microbial assay. Altogether 4.8 liters of the broth are harvested. Isolation carried out according to the method described in Example 2 yielded 2.75 g of cyclosporine A.

What we claim is:

1. A microbial process for the production of cyclosporine complex or of its components, cyclosporine A, cyclosporine B and cyclosporine C, by the aerobic fermentation of a filamentous fungus strain biosynthesizing the above antibiotic(s) in a nutrient medium containing utilizable carbon and nitrogen sources as well as mineral salts, which comprises cultivating *Tolypocladium varium* 001005 which produces the cyclosporine antibiotic complex, on a nutrient medium containing carbon sources, organic and inorganic nitrogen sources as well as mineral salts, under aerobic conditions, at 25°-30° C., and recovering said cyclosporine antibiotic complex or its components cyclosporine A, cyclosporine B and cyclosporine C.

2. A process as claimed in claim 1, wherein fermentation is carried out in a culturing medium containing pepton, ammonium sulfate and tryptone as nitrogen sources and glucose, maltose and sorbitol as carbon source.

* * * * *

UNITED STATES PATENT AND TRADEMARK OFFICE
CERTIFICATE OF CORRECTION

PATENT NO. : 5,156,960

DATED : October 20, 1992

INVENTOR(S) : JEKKEL nee BOKANY et al.

It is certified that error appears in the above-identified patent and that said Letters Patent is hereby corrected as shown below:

Column 10, line 41, "varium 001005" should read -- varium NCAIM(P)F 001005 --

Signed and Sealed this

Eighth Day of February, 1994

Attest:

BRUCE LEHMAN

*Attesting Officer*      *Commissioner of Patents and Trademarks*